United States Patent [19]

Kirksey

[11] Patent Number: 4,576,281

[45] Date of Patent: Mar. 18, 1986

[54] DISPOSABLE SYRINGE NEEDLE SEPARATION AND STORAGE BOX

[75] Inventor: Patricia E. Kirksey, Harlem, Ga.

[73] Assignee: University Hospital, Augusta, Ga.

[21] Appl. No.: 645,208

[22] Filed: Aug. 29, 1984

[51] Int. Cl.$^4$ .......................... A61M 5/32; B65F 7/00; B26F 3/00

[52] U.S. Cl. .................................... 206/370; 206/366; 206/380

[58] Field of Search ...................... 206/370, 366, 63.5, 206/380, 365, 381, 216; 225/93; 241/99

[56] References Cited

U.S. PATENT DOCUMENTS 3,469,750  9/1969  Vanderbeck ......................... 241/99
4,494,652  1/1985  Nelson et al. ......................... 206/37

Primary Examiner—William T. Dixson, Jr.
Assistant Examiner—Brenda J. Ehrhardt
Attorney, Agent, or Firm—Sughrue, Mion, Zinn, Macpeak, and Seas

[57] ABSTRACT

A vertically upright box-type outer enclosure includes a hinged, lockable front door permitting an upwardly open disposable jar container to be locked internally and aligned with a hole within the top of the box-type enclosure. A cylindrical drop chute fits to the hole and is barrel bolt locked in position with its lower end penetrating the top of the jar. The top of the drop chute carries a slotted needle remover plate, with the slot tapering such that a disposable sharp steel plastic needle holder frictionally fit to the lower end of a syringe barrel is inserted within the slot at its enlarged end, moved transversely within the slot such that the plastic needle holder is captured beneath the needle remover plate. The syringe body barrel is moved upwardly detaching the needle therefrom and permitting it to fall by gravity into the sharps impenetrable, jar type container. The door is periodically opened and the jar and accumulated needles removed.

4 Claims, 3 Drawing Figures

DISPOSABLE SYRINGE NEEDLE SEPARATION AND STORAGE BOX

FIELD OF THE INVENTION

This invention relates to a box-type sharps enclosure for accumulating separated needles or syringes after use within hospitals, and more particularly, to an improved sharps enclosure capable of separating the needle from the syringe barrel, facilitating the storage of separated needles and the disposal of the same by the utilization of a substantially impervious container eliminating any possible injuries to hospital employees.

BACKGROUND OF THE INVENTION

Sharps enclosures have been developed of stainless steel metal to safely and securely contain infectious sharps material such as syringe needles, after their use. Such lockable sharps enclosure may take the form of that manufactured and sold under the trademark SHARP SAFES by the Monoject Division of Sherwood Medical, a Brunswick Company of St. Louis, Mo. The lockable enclosure of Monoject utilizes a rectilinear parallelepiped metal container which includes a hinged door and supports internally, a removable upwardly open plastic tray. Within the tray is disposed a plastic bag whose open end is placed over the corners of the inner container and disposed beneath a convenient deposit port formed by a tubular plastic member which projects through a hole within the side or top of the outer enclosure. This permits a complete syringe with needle to be gravity dropped or laterally inserted through the tubular deposit port, whereby it falls into the plastic bag.

Periodically, a hospital employee opens the locked door, removes the inner container bearing the plastic bag within which the syringes collect, grasps the edges of the bag and rolls the edges to close the bag and places the bag in a further container or collection cart. As can be appreciated, such disposal system allows the needles to easily puncture the bags with the possibility of infection to the personnel coming into contact with the exposed sharp needle tip.

Further, due to the danger of spread of infection, while sharps such as the needle of a syringe is required to be disposed of, the barrel and plunger components of the syringe may be re-used with reprocessing. It is, therefore, advantageous to facilitate separation of the needle from the syringe barrel, further dispose of the needle, and achieve those ends without the hazzard of spreading infection.

It is, therefore, a primary object of the present invention to provide an improved sharps material disposal container which facilitates separation of the disposable needle from a syringe barrel, storage of the disposable needles in a locked manner, and which facilitates removal of accumulated needle or otherwise infectious sharps material from the container when unlocked.

SUMMARY OF THE INVENTION

The invention is directed to a vertically upright lockable outer enclosure for removably supporting an upwardly open disposable container, and wherein the enclosure includes a hole within the top thereof aligned with the opening within the upwardly open disposable container. The improvement comprises a cylindrical drop chute mounted within the hole within the top of the vertically upright outer enclosure, means for locking the chute to the enclosure in axial alignment with the disposable container opening, and wherein a syringe needle remover is carried internally of the chute having means for mechanically engaging the syringe barrel of a medicament type syringe which syringe barrel bears internally a reciprocating plunger and which barrel terminates in a plastic needle carrier concentric about and in frictional grip with the lower end of the syringe barrel. This causes separating of the needle carrier and needle from the syringe barrel upon upward pulling of the syringe barrel relative to the mechanical engaging means and to thereby cause the needle assembly to fall through the chute into the storage container.

The needle remover may comprise a thin plate spanning transversely over at least a portion of the drop chute interior, with the plate including a tapered slot, being wider at one end than the plastic needle sleeve fitted to the lower end of the syringe barrel and having an opposite short end which is smaller than the diameter of the plastic needle sleeve. The plate may be, in plan form, a hemisphere to close off approximately one-half of the drop chute passage such that the syringe barrel, plunger and needle or other infectious sharps material may be alternatively dropped into the disposable inner container through the drop chute.

The drop chute may comprise a short length plastic tube having a radially enlarged collar at its upper end with the lower end sized slightly smaller than the diameter of the hole within the top of the enclosure. With the drop chute inserted vertically within the hole, the lower end protrudes into the interior of the enclosure and the collar functions as a stop. The means for locking the chute to the enclosure may comprise a laterally slidable barrel bolt fixed to the top of the enclosure, on the inside thereof, to the side of the hole within that top, and which includes a plunger projectable within a bolt receiving hole within the bottom of the drop chute below the collar. Thus, when the enclosure is open, after the drop chute is inserted within the chute mounting hole, the barrel bolt is shifted axially so as to penetrate the bolt hole within the drop chute to securely lock the drop chute to the box-type enclosure. The disposable inner container may comprise an upwardly open plastic jar having a mouth sized slightly larger than the diameter of the lower end of the drop chute and with the length of the drop chute being such that its lower end penetrates into the mouth of the jar when the drop chute is lowered within the chute mounting hole at the top of the lockable enclosure.

DESCRIPTION OF THE PREFERRED EMBODIMENT

Figure 2:
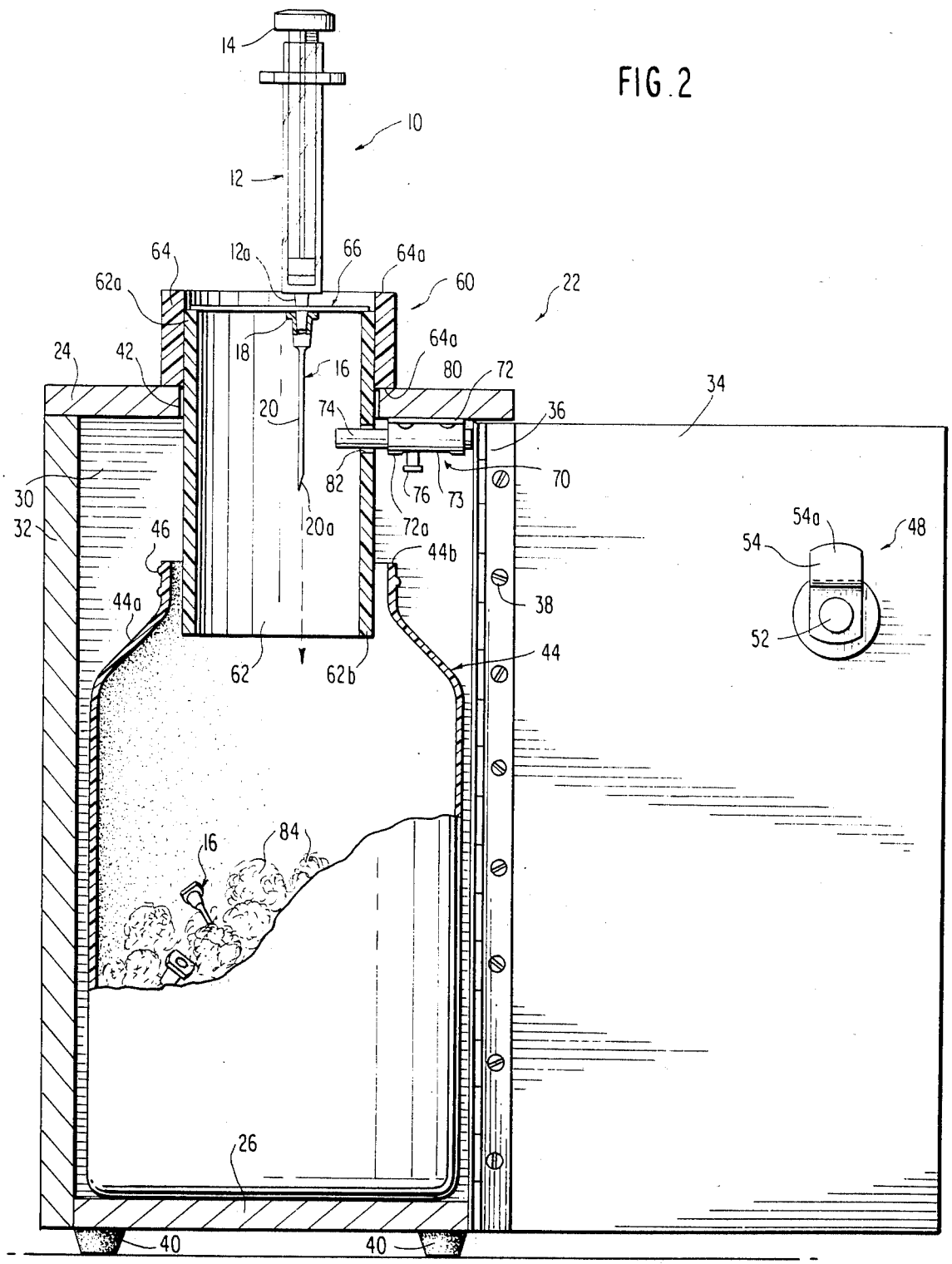
FIG. 2 is a vertical sectional view of the box of FIG. 1, taken about lines 2—2 of FIG. 3, prior to door closure.

The disposable syringe needle, lockable storage enclosure or box of the present invention functions to both facilitate the separation of a syringe needle from the syringe barrel and the storage of separated needles under tight security while additionally facilitating the removal of the accumulated needle assemblies after separation by periodic access to a removable container positioned internally of the box and for gravity receipt of the separated needle assemblies. Reference to FIG. 2 shows a typical medicament applicator syringe indicated generally at 10 comprised of a syringe barrel indicated generally at 12 within which is mounted an axially displaceable plunger 14. Barrel 12 includes a reduced diameter tip as at 12a, upon which is frictionally mounted a needle assembly indicated generally at 16, which needle assembly 16 comprises a plastic needle carrier or sleeve 18 sized slightly smaller than the tip portion of the syringe barrel and terminating at its lower end in a sharpened steel needle 20.

Such syringes are common and, while being disposable themselves, permit by the separation of the frictional grip of the needle mounting sleeve 18 from the barrel 12, the re-use or reprocessing of the syringe barrel and plunger components. Since the needle 20 must penetrate the skin of the patient, it constitutes a readily infectious sharps material element which requires careful handling and ultimate disposal without the possibility of contacting hospital personnel.

In that respect, the present invention is directed to a separated syringe needle storage enclosure or box for facilitating the disposal of such needles after separation from the syringe barrel with such enclosure having means for facilitating the separation thereof. Further, it should be appreciated that certain components of the enclosure and disposal elements have counterparts in the referred to prior art apparatus. The improved, vertically upright, syringe needle storage enclosure box for facilitating the disposal of such separated needles, is indicated generally at 22. The vertically upright, outer box may be formed of steel although the illustrated box is of wood. In that respect, the enclosure 22 includes a top wall 24, a bottom wall 26, laterally opposed sidewalls 28 and 30, a rear wall 32 and a front opening door 34. The door 34 is mounted to the right sidewall 30 by way of a continuous hinge 36, the hinge 36 being appropriately screwed to the end of sidewall 30 and to the end of the door 34 by means of wood screws 38. Rubber grommets at 40 are fixedly mounted to the lower surface of the bottom wall 26 to permit the enclosure 22 to stand upright on the surface of a desk, cabinet or the like. Enclosure 22 is essentially identical to the cited prior art outer enclosure, and may be made of steel or other sheet metal in the manner of the prior art structures, if desired.

Additionally, the top wall 24 is provided with a circular opening or hole 42. Unlike the prior art, instead of a basin or dish bearing a plastic bag functioning as the inner container for receiving separated disposable syringe needles or needle assemblies, which are gravity dropped into such container, the present invention employs a molded plastic jar indicated generally at 44 which is of a diameter approximating the width of the enclosure 22, and enclosure 22 may be square in cross-section. Further, the height of the jar 44 is such that it does not reach to the top wall 24 of the outer enclosure 22. The plastic jar 44 is necked down at its upper end as at 44a, terminating in a reduced diameter throat or rim 44b, which throat or rim 44b is threaded on its outer surface as at 46. As such, when a sufficient quantity of needle assemblies 16 accumulate within the jar 44, the door 34 may be unlocked, the jar 44 removed, and a cap (not shown) threaded to the top of the jar, The cap may be metal or plastic but should be sufficiently strong to prevent the sharp point 20a of the metal needle 20 from penetrating through the wall of the plastic jar 44 or its cap (not shown).

Figure 1:
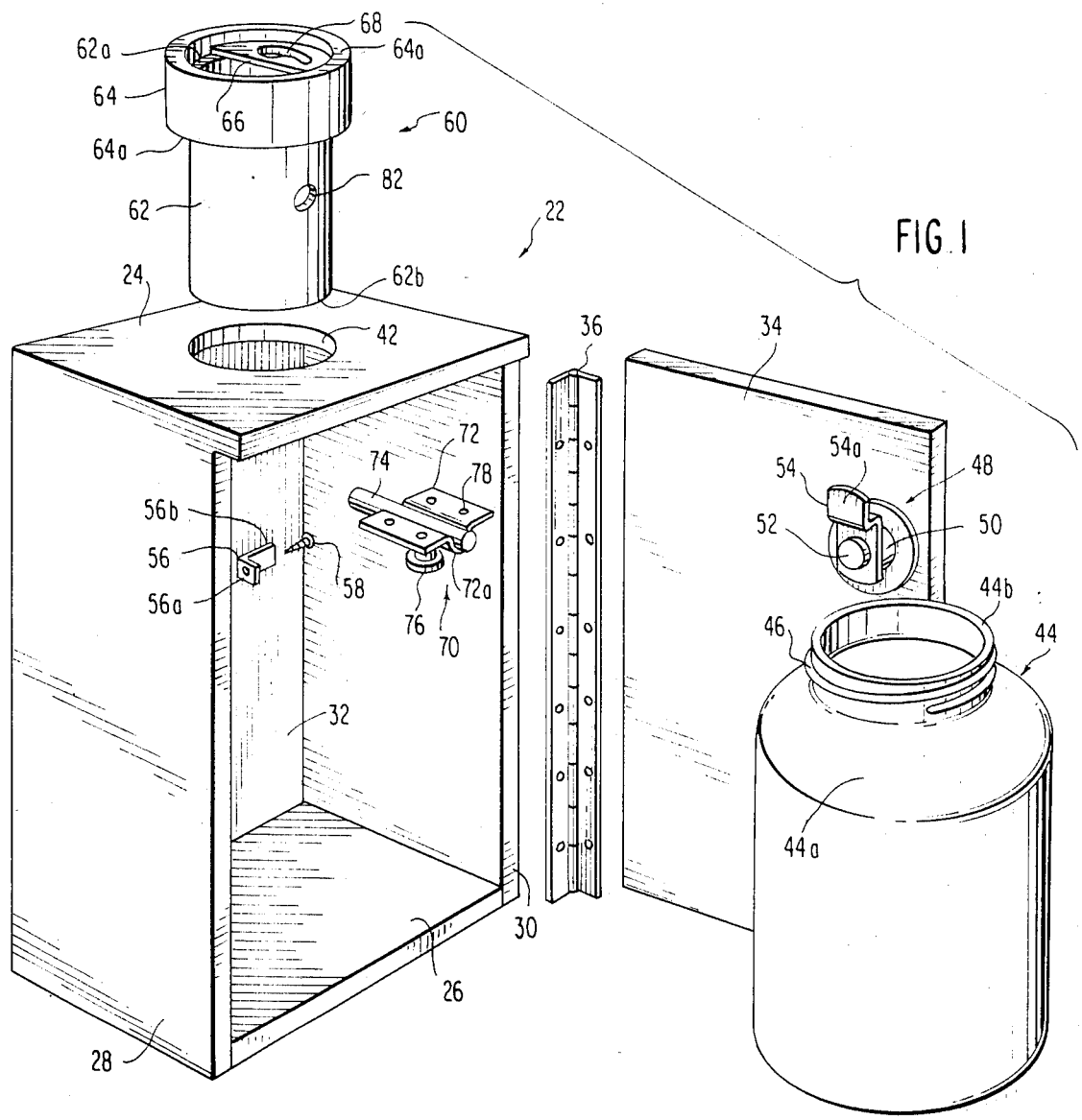
FIG. 1 is an exploded perspective view of the disposable syringe needle separation and storage box forming a preferred embodiment of the present invention.
Figure 3:
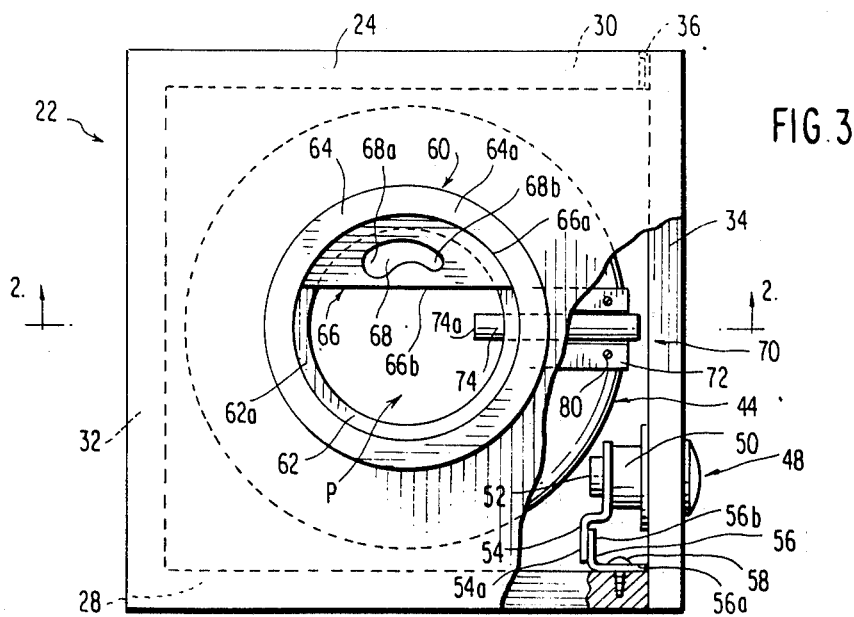
FIG. 3 is a top plan view, partially broken away, of the box of FIGS. 1 and 2.

In the manner of the prior art outer enclosure, the door 34 may be locked in closed position once the inner container or jar 44 is positioned therein. In that respect, there is provided a key lock indicated generally at 48 which includes a barrel portion 50 penetrating the thickness of door 34 and bearing a rotatable pin 52 internally, to which is fixed a radially projecting, sheet metal latch 54. Mounted to the inside of left sidewall 28 is an L-shaped metal catch 56, the base 56a of which is screw mounted to the interior surface of sidewall 28 by means of screws 58, while the right angle leg 56b projects outwardly of the sidewall 28. The position of the catch 56 is such, with respect to pivotable latch 54, and the configuration of the latch is such that an offset portion 54a of the latch 54 moves behind the leg 56b of catch 56 when rotated 90 degrees from the position shown in FIG. 1 to securely lock the door 34 in closed position. This prevents access to the accumulated needle assemblies 16 within the upright, open jar 44.

Important to the present invention, is the utilization of a drop chute indicated generally at 60 which performs multiple functions. The drop chute 60 is comprised of a short length plastic tube 62 which has an outside diameter slightly less than the diameter of the chute mounting hole 42 within top wall 24 of the outer enclosure. Further, the chute 62 has mounted at its upper end 62a and concentrically adhesively attached, an enlarged diameter collar 64 whose upper edge 64a projects above the upper edge 62a of tube 62, so as to form a rest for a platelike needle extractor or remover, indicated generally at 66. The needle extractor 66 is formed of sheet metal and is in the shape of a half moon plate in plan configuration, having an arcuate outer edge 66a whose radius of curvature corresponds to that of the inner periphery of collar 64. Between the curved edge 66a and the staight edge 66b, there is provided a tapered, irregular slot 68 which includes a large width portion 68a which is generally circular in cross-section and a narrowed, section 68b, as an extension thereof. The needle extractor 66 may be adhesively fixed to the end 62a of tube 62 with the curved periphery 66a abutting the inner periphery of collar 64 and being adhesively bonded thereto, all by means of the same adhesive which bonds collar 64 to tube 62 at its upper end.

The length of the tube 62 is such that the lower edge 62b thereof penetrates into the throat 44b of jar 44 and the throat 44b is of a diameter in excess of the outer diameter of tube or chute 62 to permit that insertion. Further, the length of collar 64 and its position on tube 62 defines the extent of penetration of tube 62 through chute mounting hole 42 with the lower edge 64b of the collar resting on the top wall 24, FIG. 2.

The present invention utilizes means for mechanically locking the drop chute 60 to enclosure 22 after insertion of the drop chute tube 62 into the chute mounting hole 42. The locking means utilizes a barrel bolt indicated generally at 70 which may comprise a commercially available sliding bolt formed by a sheet metal plate 72 which is bent into U-shape at its center at 72a to form a semi-cylindrical cavity bearing an axially slidable bolt or locking pin 74. The U-shaped portion of the plate 72 includes an elongated slot 73 through which projects an actuator knob 76 fixed to pin 74 and projecting at right angles thereto. Mounting holes 78 are provided within plate 72 on opposite sides of the pin 74, through which project suitable screws as at 80, with the screws mounting the plate 72 flush against the bottom surface of outer enclosure top wall 24. Access to the barrel bolt 70 may be had by opening door 34. Additionally, a bolt receiving hole 82 is formed within tube 62 at a predetermined distance below lower edge 64b of collar 64, and during insertion of the drop chute 60, the hole 82 is maintained in a position facing the door 34 and aligned with the slidable bolt or pin 74. The bolt hole 82 is slightly larger in diameter than the diameter of the bolt or locking pin 74 such that end 74a of pin 74 is projectable into the bolt receiving hole 82 after lower edge 62b of the tube 62 penetrates the interior of the jar 44 at throat 44b.

Under such conditions as seen in FIG. 2, with container 44 locked internally of enclosure 22 by locking of door 34, and with the barrel bolt 70 in the position shown in FIG. 2, the drop chute is mechanically latched to top wall 24 of the outer enclosure 22. By physically placing the syringe 10 in the position shown in FIG. 2, with the needle assembly 16 penetrating fully the enlarged portion 68a of the slot 68 within the needle extractor plate 66 and by sliding the reduced diameter tip portion 12a of the syringe plastic barrel 12 into the narrowed portion 68b of the slot 68, an upward pull on the barrel 12 will cause the separation of the frictionally gripped needle mounting sleeve 18 from the reduced diameter tip portion 12a of the plastic barrel 12, thereby separating the needle assembly 16 from the barrel and plunger components of the syringe 10. Once this is achieved, the needle assembly 16 falls as indicated by the dotted line arrow, under gravity influence, into the open top jar 44. Preferably, cotton balls or batting 84 fill the bottom of the jar 44 to cushion the fall of the needle assemblies 16 and to resist any possible tendency of the sharp tip 20a of a detached needle assembly 16 from possibly penetrating the plastic jar 44.

It should be noted that plate 66 does not completely cover the deposit port P defined by the upper end 62a of tube 62 of the drop chute 60. There is considerable space to the side of the straight edge 66b of needle extractor plate 66 which permits the passage of infectious sharps material other than the separated needle assemblies 16 from syringes 10 to pass therethrough for deposit and accumulation within the interior of the plastic jar 44.

In like manner to the prior art, periodically hospital personnel may open door 34, after unlocking, and, upon bolt release of the drop chute 60, it may be lifted up or even removed from the top wall 24 of enclosure 22, to allow the jar 44 bearing the infectious sharps material may be removed through open door 34. The jar after capping of the accumulated infectious sharps material therein, may then be disposed of in accordance with hospital procedures.

From the above, it should be evident that the needle storage box or enclosure 22 of the present invention utilizes a substantially impervious inner container or plastic jar into which the infectious sharps objects are dopped. Thus, during removal of the relatively rigid-wall jar 44, there is no possibility of the needle tips or other sharp objects penetrating through the wall of the jar and that the hospital attendant fully complies with typical hospital instructions requiring that the accumulated needles be removed while keeping personnel's hands away from sharps.

Further, while the components of the needle separation and storage box 22 are shown as comprising a wooden exterior enclosure 22 and having the balance of the components other than barrel bolt 70 and key lock assembly 48 formed of metal, along with hinge 36, the balance of the components borne by the box 22, integrated thereto or detachably mounted thereto, may be formed of plastic including needle extractor plate 66 of the drop chute 60.

While the invention has been particularly shown and described with reference to a prefrred embodiment thereof, it will be undestood by those skilled in the art that various changes in form and details may be made therein without departing from the spirit and scope of the invention.

What is claimed is:

1. A disposable syringe needle separation and storage box comprising a vertically upright outer enclosure, said outer enclosure including an externally lockable door for providing access to the interior thereof, an upwardly open syringe needle storage and disposal container positioned therein through said lockable door when open, said enclosure including a hole within the top thereof aligned with the open end of the upwardly open container, the improvement comprising:

a tubular drop chute, removably axially positioned within said hole within the top of said enclosure, means internally of said storage box for locking said tubular drop chute to said enclosure in alignment with said container opening, a needle extractor fixedly mounted to the interior of said tubular chute, said needle extractor comprising a slotted plate at least partially closing off the interior of said drop chute, said plate including a tapered slot having a portion sized in excess to the diameter of the needle to permit manual penetration of the needle into said drop chute, below said extractor plate, permitting lateral movement of the sytinge to a position where the upper end of the needle contacts the bottom of said slotted plate, whereby, the syringe barrel may be separated from the needle through single hand manipulation, movement laterally within the tapered slot, and by single handed pull of the syringe upwardly to separate the needle, such that the needle falls by gravity into the interior of said container;

whereby, when said syringe needle separation and storage box is in use, said tubular drop chute cannot be removed, since it is latched from the inside, and its removal from said needle separation and storage box and the removal of the disposal container bearing sharps can be accomplished only by unlocking the door, and unlocking of said drop chute from the storage box, thereby insuring the safety of the system.

2. The box as claimed in claim 1, wherein said hole is circular, said drop chute comprises a cylindrical tube having an outer diameter slightly less than the diameter of the hole within the top of the enclosure, said drop chute comprises a radially enlarged collar at its upper end, and wherein the upper end of said collar projects above the upper end of said tube and is fixed thereto, and wherein said needle extractor comprises a thin plate having an outer periphery of a diameter matching the inner diameter of said collar and said needle etractor plate rests on the upper end of said tube and is fixed thereto.

3. The box as claimed in claim 2, wherein said tube includes a hole passing radially therethrough at a point below the lower edge of said collar, said inner container comprises an upright jar terminating in a tapered throat, said tube is of a length such that the lower end of the tube projects within said tapered throat when said drop chute is mounted to said enclosure with the container in place, and wherein said means for locking said drop chute to said enclosure comprises a laterally projectable barrel bolt mounted to the interior of said enclosure top, adjacent to the hole receiving said drop chute, and wherein the bolt is aligned with and positioned so as to partially project into the radial hole within the side of said tube such that the tube is mechanically locked to the enclosure by operation of said barrel bolt.

4. The box as claimed in claim 3, wherein said enclosure comprises a rectangular rectilinear parallelepiped structure including a hinged door, a key lock assembly mounted to said door, a door catch fixedly mounted to the interior of said enclosure and engageable by a latch of the key lock assembly for permitting said door to be locked in closed position, and wherein said barrel bolt is fixedly mounted to the top of said enclosure adjacent to the opening formed by said hinged door and is readily accessible from the outside when said hinged door is open to facilitate locking of said drop chute after placement of the jar in vertical upright position within the interior of the said outer enclosure.

* * * * *